(12) United States Patent
Fröhlich et al.

(10) Patent No.: US 7,706,986 B2
(45) Date of Patent: Apr. 27, 2010

(54) APPARATUS FOR DETERMINING AND/OR MONITORING VOLUME AND/OR MASS FLOW OF A MEDIUM

(75) Inventors: Thomas Fröhlich, Munchenstein (CH); Achim Wiest, Weil am Rhein (DE); Andreas Berger, Therwil (CH); Harald Stocker, Schopfheim (DE); Torsten Strunz, Basel (CH); Aurele Fleury, Aesch (CH); Oliver Berberig, Schworstadt (DE); Klaus Bussinger, Munchenstein (CH); Patrick Oudoire, Soultz (FR); Saul Jacobson, Basel (CH); Frank Wandeler, Baden-Dattwil (CH); Oliver Brumberg, Rheinfelden (DE)

(73) Assignee: Endress + Hauser Flowtec AG, Reinach (CH)

( * ) Notice: Subject to any disclaimer, the term of this patent is extended or adjusted under 35 U.S.C. 154(b) by 0 days.

(21) Appl. No.: 11/411,857

(22) Filed: Apr. 27, 2006

(65) Prior Publication Data

US 2006/0278016 A1 Dec. 14, 2006

(30) Foreign Application Priority Data

May 9, 2005 (DE) .................. 10 2005 022 048

(51) Int. Cl.
*G01F 1/00* (2006.01)
(52) U.S. Cl. .................. 702/48; 702/54; 73/861.25; 73/861.31

(58) Field of Classification Search ............ 702/45, 702/48–40, 54; 73/861, 861.18, 861.19, 73/861.25–861.29, 861.31
See application file for complete search history.

(56) References Cited

U.S. PATENT DOCUMENTS

| 5,228,347 | A | * | 7/1993 | Lowell et al. ............ 73/861.28 |
| 7,117,104 | B2 | * | 10/2006 | Urdaneta et al. ............ 702/48 |
| 2002/0011120 | A1 | * | 1/2002 | Huang ..................... 73/861.25 |
| 2004/0020296 | A1 | * | 2/2004 | Moles et al. ................. 73/627 |
| 2007/0039399 | A1 | * | 2/2007 | Groeschel ............... 73/861.27 |

FOREIGN PATENT DOCUMENTS

JP 61023920 A * 2/1986

* cited by examiner

*Primary Examiner*—Manuel L Barbee
(74) *Attorney, Agent, or Firm*—Bacon & Thomas, PLLC

(57) ABSTRACT

An ultrasonic flow measuring device, which determines volume and/or mass flow of a medium in a pipeline, or in a measuring tube. The flow measuring device includes a plurality of ultrasonic sensors, which emit and/or receive ultrasonic measurement signals along defined sound paths. The control/evaluation electronics of the flow measuring device is divided into an on-site electronics, in which at least one switch is provided, via which the ultrasonic sensors, arranged in different sound paths, can be driven and/or queried, and at least one remote, control/evaluation unit, wherein the control/evaluation unit so switches the at least one switch, that the driven and/or queried, ultrasonic sensor, or the driven and/or queried pair of ultrasonic sensors, is activated and provides measured values.

5 Claims, 1 Drawing Sheet

APPARATUS FOR DETERMINING AND/OR MONITORING VOLUME AND/OR MASS FLOW OF A MEDIUM

FIELD OF INVENTION

The invention relates to an apparatus for determining and/or monitoring volume and/or mass flow of a medium flowing through a pipeline, or measuring tube, as the case may be. The apparatus includes a plurality of ultrasonic sensors, which emit (or send) and/or receive the ultrasonic measurement signals along defined sound paths, and a control/evaluation unit, which determines the volume and/or mass flow of the medium in the pipeline, or in the measuring tube, on the basis of the ultrasonic measurement signals using a sound-entrainment method or the echo principle.

BACKGROUND OF INVENTION

Known ultrasonic flow measuring devices are composed of a driver/evaluation electronics and ultrasonic sensors, which convert the electrical signal into ultrasonic measurement signals, and vice versa. If ultrasonic flow measuring devices are used for highly accurate measurements, then it is unavoidable that the measurements must be performed in a plurality of channels, or over a plurality of sound paths. By means of measurement on a plurality of sound paths, it is possible to determine, with sufficient accuracy, the actual flow profile, and thus the actual flow velocity, of the medium through a pipeline, or through the measuring tube, as the case may be.

For the purpose of driving the ultrasonic sensors and for evaluation of the ultrasonic measurement signals sent and received by the ultrasonic sensors, it is necessary that the electric signals be brought to and from each of the individual ultrasonic sensors. In many cases of application, the electronics is, in such case, spatially separated from the measuring location, where the ultrasonic sensors are located. Separations of up to about 100 m are not uncommon. The electrical wiring is provided, usually, in the form of coaxial, or triaxial, cable—thus very high quality and, consequently, expensive, cable. These cables are distinguished by a very good shielding of the relatively weak, electrical signals, especially of the received signals; however, they are relatively expensive. Desirable, in view of this background, is a reduction of the costs for the wiring between the electronics, where the interaction capability and display are located, and the ultrasonic sensors.

SUMMARY OF INVENTION

An object of the invention is to provide a cost-favorable, ultrasonic, flow measuring device utilizing multiple sound paths.

The object is achieved by providing an on-site electronics, in which at least a first switch is provided, via which the ultrasonic sensors, located in different sound paths, are drivable and/or queryable, and by providing at least one remote, control/evaluation unit, with the control/evaluation unit so switching the first switch, that the driven and/or queried ultrasonic sensor, or the driven and/or queried pair of ultrasonic sensors, is activated, and provides, measured values.

In short, the solution of the invention is distinguished by a time multiplexing of the electrical signals of the ultrasonic sensors. At the actual location of measurement, i.e. at the measuring tube, or at the pipeline, with, in the case of use of the travel-time difference method, ultrasonic sensors arranged in pairs, there is, along with the passive components, which convert the electrical signals into sound, and vice versa, additionally, a switch provided. According to a further development of the apparatus of the invention, the on-site electronics and the control/evaluation unit are connected together via at least one connecting line.

In a preferred embodiment of the apparatus of the invention, it is provided, that a second switch and a synchronizing unit are assigned to the control/evaluation unit. In this way, also the evaluating electronics, or the on-site electronics, as the case may be, has available a switch and a synchronization circuit for setting the switch position of the measuring location. This is enabled by having, according to the invention, always only one ultrasonic sensor active. Thus, of the plurality of ultrasonic sensors, only the first ultrasonic sensor of a pair can send; displaced in time, the second ultrasonic sensor assigned to the first ultrasonic sensor receives the ultrasonic measurement signal of the first ultrasonic sensor. Successively in a measurement cycle, thus each ultrasonic sensor is activated twice, once as an emitter and once as a receiver. A measuring cycle, in which the ultrasonic sensors, in effect, serially sample the flow profile, is also quite sufficiently fast, since it can be assumed that the flow profile and the flow velocity of the medium being measured will not change significantly during a measurement cycle. Preferably, the frequencies of the switching lie below 10 kHz; in this way, it is possible to use more cost-favorable, low-frequency cable. In contrast, the usual frequencies for the ultrasonic measurement signals lie in the range of several MHz. At least, however, the ultrasonic measurement signals have a frequency greater than 100 kHz.

An advantageous further development of the apparatus of the invention provides, additionally, an input unit, via which the switching frequency of the first switch and/or of the second switch is so selectable, that the switching frequency can be optimized as a function of the particular system and/or process-specific variables.

A further simplification can be a shifting of the driver, or sending stage, of the ultrasonic sensors to the measuring location. In this case, then only one high-value cable is needed for connecting the measuring location and the evaluating electronics. High-value means, in this case, that the cable has very good shielding and a low amount of damping. The information transfer to the location of the switch can be effected via inexpensive signal lines. It is also possible to transfer the information to the location of the switch serially, so that the number of lines can then be reduced still further.

Alternatively, it is, of course, possible to provide a first electric connecting line between the control/evaluation unit and the on-site electronics for the sending operation of the ultrasonic sensors and to provide a second electric connecting line between the control/evaluation unit and the on-site electronics for the receiving operation of the ultrasonic sensors. Preferably, the connecting line includes both shielded and non-shielded cores.

BRIEF DESCRIPTION OF THE DRAWINGS

The invention will now be explained in greater detail on the basis of the appended drawings, the figures of which show as follows:

FIG. 1 shows a schematic drawing of a first form of embodiment of the ultrasonic flow measuring device 9. Ultrasonic flow measuring device 9 is either an inline flow measuring device, wherein the ultrasonic sensors 1 are integrated into the wall of a measuring tube 2, or it is a clamp-on flow measuring device, wherein the ultrasonic sensors 1 are affixed externally on the pipeline 2 via a securement mechanism.

DESCRIPTION OF THE PREFERRED EMBODIMENTS

Figure 1:
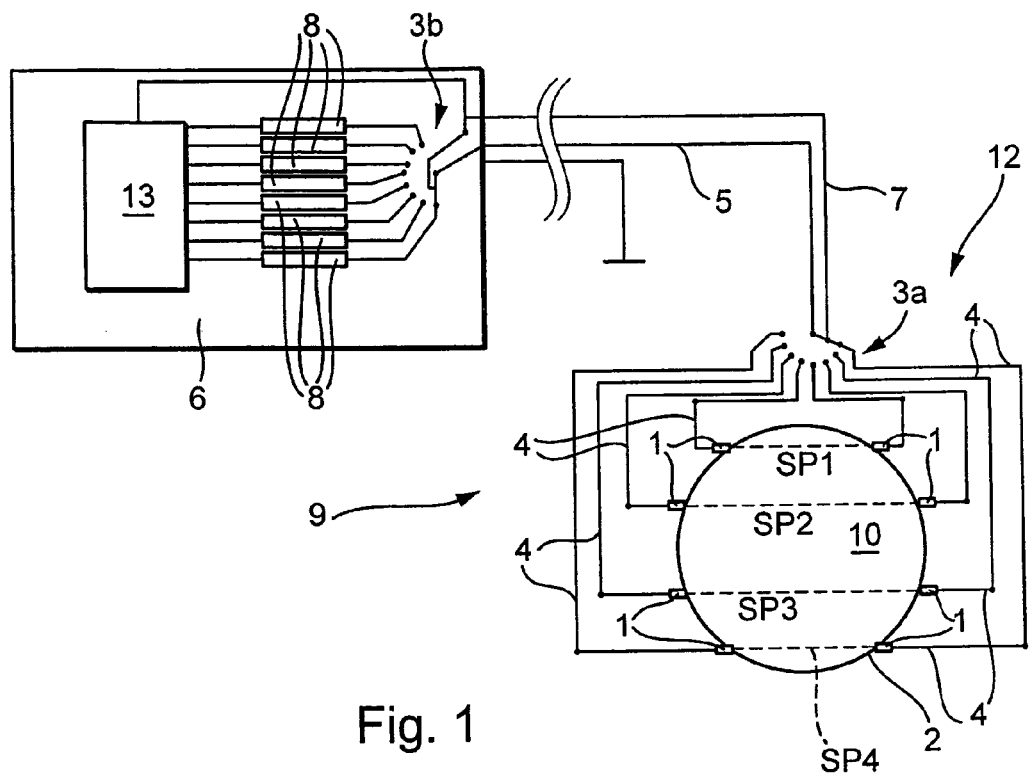
FIG. 1 a schematic drawing of a first form of embodiment of the apparatus of the invention.

In order to be able to determine the flow profile of the medium 10 flowing in the pipeline 2, or in the measuring tube, four pairs of ultrasonic sensors 1 are arranged on the pipeline 2, or on the measuring tube, distributed around the periphery thereof. The flow velocity, or the volume, or mass, flow rate, through the pipeline 2, or through the measuring tube, is determined, in the illustrated case, via a travel time difference method, from the ultrasonic measuring signals, which pass through the measured medium 10 in, and against, the stream direction of the measured medium 10.

The electronics for driving the ultrasonic sensors 1 and for evaluating the travel time difference of the ultrasonic measurement signals is divided, according to the invention, into an on-site electronics, with the switch 3a, which is directly associated with the measuring location, i.e. with the measuring tube 2 and its ultrasonic sensors 1, and a remote, control/evaluation unit 6, which contains the switch 3b. The remote, control/evaluation unit 6 is preferably also provided with a unit 11 enabling interaction therewith.

According to the invention, a time multiplexing of the electrical signals of the ultrasonic sensors 1 is performed. At the actual location of measurement, i.e. at the measuring tube 2, or the pipeline, with the, in the case where the travel time difference method is being used, ultrasonic sensors 1 arranged in pairs, there is, along with the passive components, which convert the electrical signals into sound, and vice versa, additionally the switch 3a. The on-site electronics and the control/evaluation unit 6 are connected together via the connecting line 5. This connecting line is a high-value line, since the emitted signals, but especially the relatively weak, received signals, must be transferred disturbance-free over it. In addition to the high-value, connecting line, the illustrated example also is provided with the connecting line 7 between the switch 3a in the on-site electronics and the switch 3b in the control/evaluation unit 6. Via the switch 3b, the emitting/receiving units 8 associated with the individual ultrasonic sensors 1 are actuated. Connecting line 7, which serves for synchronizing the switch 3a in the on-site electronics and the switch 3b in the control/evaluation unit 6, can be a cost-favorable cable.

Via the input/interaction unit 11, it is possible to so select the switching frequency of the first switch 3a and/or that of the second switch 3b, that the switching frequency can be optimized as a function of the particular system and/or process-specific variables. Preferably, the switching frequency lies below 10 KHz; in this way, it is possible to use cost-favorable, low-frequency cable. Due to the relatively slow changes of the flow profile, this switching frequency suffices for an adequate accuracy of measurement of the volume flow. The frequency of the ultrasonic measurement signals lies, in contrast, in the order of magnitude of several MHz. At least, the ultrasonic measurement signals have a frequency of greater than 100 kHz.

Figure 2:
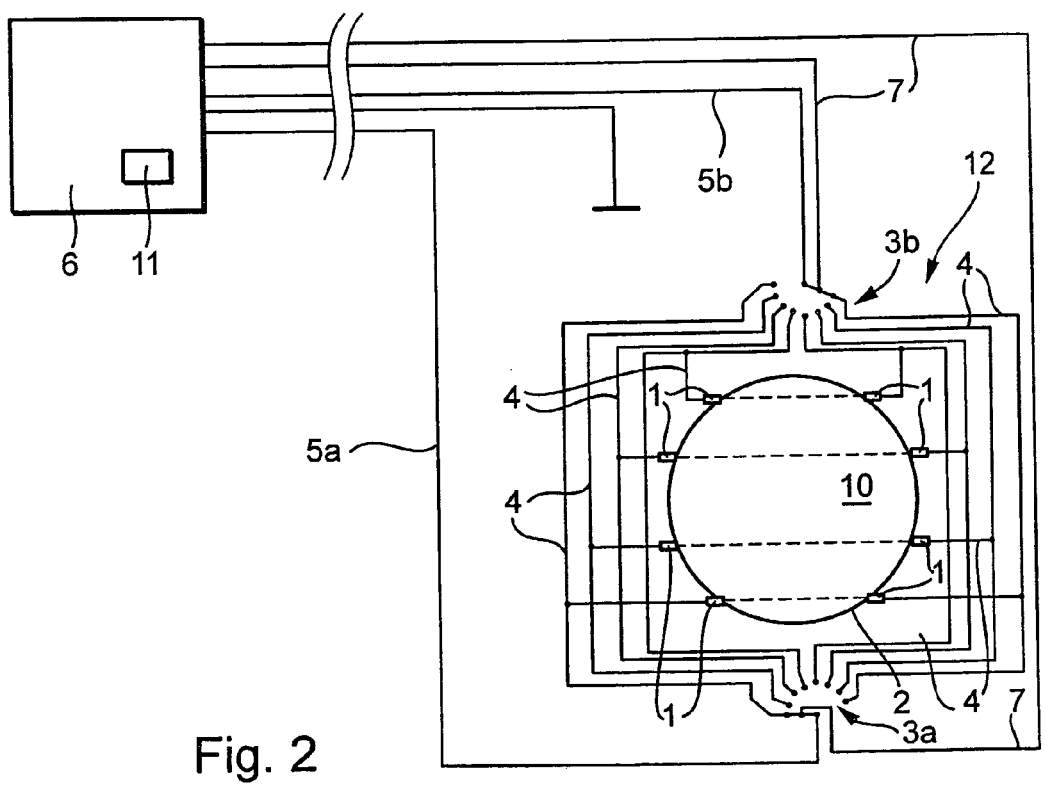
FIG. 2 a schematic drawing of a second form of embodiment of the apparatus of the invention.

FIG. 2 is a schematic drawing of a second form of embodiment of the ultrasonic flow measuring device 9 of the invention. This form of embodiment differs from the form of embodiment shown in FIG. 1 by the integration of the two switches 3a, 3b into the on-site electronics. In this case, it is sufficient to use relatively weakly shielded cable for the connecting lines 4, since only crosstalk between the individual cables must be prevented. In this way, it becomes possible to use relatively cost-favorable cable for the connections between the switches 3a, 3b and the ultrasonic sensors 1. Only for the connection of the measurement location to the control/evaluation unit is it still required to apply at least one cost favorable cable 7 and high value cables 5a and 5b, for transmission of the emitted and/or received signals.

The invention claimed is:

1. An apparatus for determining and/or monitoring volume and/or mass flow of a medium flowing in a stream-direction through a pipeline, or measuring tube, comprising:

a measurement location having a plurality of ultrasonic sensors, which emit and/or receive ultrasonic measurement signals along defined sound paths;

a control/evaluation unit, which determines volume and/or mass flow of the medium in the pipeline, or in the measuring tube, on the basis of the ultrasonic measurement signals, using a sound-entrainment method;

on-site electronics, in which at least a first switch is provided, via which the ultrasonic sensors arranged in different sound paths are drivable and/or queryable, a second switch, which is assigned to said control/evaluation unit, via which emitting/receiving units associated with the individual ultrasonic sensors are actuated;

a first, high quality electrical connecting line between said on-site electronics and said control/evaluation unit for transferring the emitted and received signals; and a second electrical connecting line between said control/evaluation unit and said on-site electronics, serving for synchronization of the switches in the on-site electronics and in the control/evaluation unit wherein:

said control/evaluation unit is provided with an input unit and is remotely located relative to said measurement location and switching said at least said first switch, that the driven and/or queried, pair of ultrasonic sensors, is activated and provides measured values.

2. The apparatus as claimed in claim 1, further comprising:

a synchronizing unit assigned to said control/evaluation unit.

3. The apparatus as claimed in claim 2, wherein:

said first high-quality electrical connecting line comprises shielded cable.

4. The apparatus as claimed in claim 1, wherein:

the frequency of said ultrasonic measurement signal is greater than 100 kHz and the switching frequency of said first switch is smaller than 10 kHz.

5. The apparatus as claimed in claim 1, further comprising:

an input unit, via which the switching frequency of said first switch and/or said second switch can be so selected, wherein:

the switching frequency is optimized as a function of particular system-and/or process-specific variables.

* * * * *